United States Patent
Pressman et al.

(10) Patent No.: US 10,398,347 B2
(45) Date of Patent: Sep. 3, 2019

(54) SHEATH VISUALIZATION METHOD BY MEANS OF IMPEDANCE LOCALIZATION AND MAGNETIC INFORMATION

(71) Applicant: BIOSENSE WEBSTER (ISRAEL) LTD., Yokneam (IL)

(72) Inventors: Assaf Pressman, Pardes Hanna-Karkur (IL); Shaul Haim Raz, Shimshit (IL); Avigdor Rosenberg, Kiryat Tivon (IL); Dror Berman, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 759 days.

(21) Appl. No.: 14/974,878

(22) Filed: Dec. 18, 2015

(65) Prior Publication Data
US 2017/0172455 A1    Jun. 22, 2017

(51) Int. Cl.
| | | |
|---|---|---|
| *A61B 5/00* | (2006.01) | |
| *A61B 5/06* | (2006.01) | |
| *A61B 5/042* | (2006.01) | |
| *A61B 5/0432* | (2006.01) | |
| *A61M 25/01* | (2006.01) | |
| *A61M 25/06* | (2006.01) | |

(52) U.S. Cl.
CPC ............ *A61B 5/063* (2013.01); *A61B 5/0422* (2013.01); *A61B 5/0432* (2013.01); *A61B 5/062* (2013.01); *A61M 25/0127* (2013.01); *A61B 5/6852* (2013.01); *A61B 5/6885* (2013.01); *A61B 5/746* (2013.01); *A61M 2025/0166* (2013.01); *A61M 2025/0681* (2013.01)

(58) Field of Classification Search
CPC .......... A61B 5/06; A61B 5/061; A61B 5/063; A61B 5/053; A61B 5/0538; A61B 5/062; A61B 5/0422; A61B 5/0432; A61B 5/6852; A61B 5/6885; A61B 25/0127; A61B 2025/0166; A61B 2025/0681
See application file for complete search history.

(56) References Cited

U.S. PATENT DOCUMENTS

| | | |
|---|---|---|
| 6,226,542 B1 | 5/2001 | Reisfeld |
| 6,301,496 B1 | 10/2001 | Reisfeld |
| 6,814,733 B2 | 11/2004 | Leatham et al. |
| 6,892,091 B1 | 5/2005 | Ben-Haim et al. |
| 6,997,924 B2 | 2/2006 | Schwartz et al. |
| 7,156,816 B2 | 1/2007 | Schwartz et al. |

(Continued)

FOREIGN PATENT DOCUMENTS

WO    2662015 A1    11/2013

OTHER PUBLICATIONS

European Search Report dated May 18, 2017 from corresponding European Patent Application No. 16204673.4.

*Primary Examiner* — Max F Hindenburg
(74) *Attorney, Agent, or Firm* — Vincent J. Serrao (57) ABSTRACT

Catheterization is carried out by inserting a sheath into a human patient and moving a catheter having an electrode through the sheath lumen. A variation between a first threshold value and a second threshold value in electrical current through the electrode is identified. Responsively to the variation, it is reported that a portion of the catheter has transitioned between an in-sheath condition and an out-of-sheath condition. The sheath is defined and identified by the historical data of the readings of the magnetic sensor during its movements.

7 Claims, 7 Drawing Sheets

(56) References Cited

U.S. PATENT DOCUMENTS

| | | |
|---|---|---|
| 7,536,218 B2 | 5/2009 | Govari et al. |
| 7,756,576 B2 | 7/2010 | Levin |
| 8,478,383 B2 | 7/2013 | Bar-Tal et al. |
| 9,693,820 B2 * | 7/2017 | Potter .................... A61B 5/062 |
| 9,724,014 B2 * | 8/2017 | Hill ........................ A61B 5/065 |
| 10,058,669 B2 * | 8/2018 | Razavi .............. A61M 16/0488 |
| 2013/0303886 A1 | 11/2013 | Ludwin et al. |
| 2015/0126895 A1 | 5/2015 | Lichtenstein |
| 2015/0223724 A1 | 8/2015 | Hauck et al. |
| 2015/0305680 A1 | 10/2015 | Curran et al. |

* cited by examiner

SHEATH VISUALIZATION METHOD BY MEANS OF IMPEDANCE LOCALIZATION AND MAGNETIC INFORMATION

BACKGROUND OF THE INVENTION

1. Field of the Invention

This invention relates to instruments for performing medical examinations of the interior of cavities. More particularly, this invention relates to instruments employing magnetic fields and impedance measurements for determining a position of a probe in the interior of a cavity.

2. Description of the Related Art

The meanings of certain acronyms and abbreviations used herein are given in Table 1.

TABLE 1

| Acronyms and Abbreviations | |
|---|---|
| ACL | Active Current Location |
| CPM | Current Position Map |

In a number of medical procedures a probe is inserted into a patient through a sheath. Typically the sheath acts to guide the probe during its insertion, as well as to maintain the probe in a desired alignment. Once the probe and the sheath have been inserted into the patient, their distal ends are not visible, so that an operator performing the procedure may be unaware of the relationship of the sheath's distal end relative to the probe's distal end. It is possible to use fluoroscopy to locate the sheath, but at the cost of exposing, which exposes the subject to radiation.

Impedance-based position sensing is one method used to guide the tip of the catheter to the target position in which the medical procedure is to be performed. Commonly assigned U.S. Patent Application Publication No. 20150126895, which is herein incorporated by reference, describes a sheath having an outer wall that surrounds an inner lumen and has multiple holes along the tube penetrating the outer wall. Multiple electrically conducting elements are inserted in the respective holes, so as to allow transmission of electrical current between the inner lumen and an exterior of the outer wall.

SUMMARY OF THE INVENTION

In one cardiac catheterization technique, the operator first inserts a sheath having ACL electrodes percutaneously into the patient's body and guides the sheath's distal end to the target region. The operator then inserts a hybrid catheter having magnetic and ACL sensors into the lumen of the sheath and guides the tip of the catheter through the sheath. When the catheter has exited the sheath, a current position map is eventually built as part of the medical procedure.

According to disclosed embodiments of the invention, data from magnetic sensors is used to trace the location of the catheter through the sheath. Once the distal portion of the catheter emerges from the sheath, the magnetic data is augmented by data from using the ACL sensors of the catheter. However the ACL data is not valid while the catheter tip is still within the sheath. By evaluating the currents in the ACL sensors of the catheter it is possible to detect the emergence of the catheter through the tip of the sheath. The combined magnetic and ACL data then locates the sheath tip prior to construction of the map.

There is provided according to embodiments of the invention a method, which is carried out by inserting a sheath into a human patient and moving a catheter through the lumen of the sheath, wherein the catheter has at least one electrode disposed on its distal portion. The method is further carried out by measuring electrical current through the electrode with current-measuring circuitry, identifying a variation in the electrical current between a first threshold value and a second threshold value, and responsively to the variation, reporting that a portion of the catheter has transitioned between an in-sheath condition and an out-of-sheath condition.

According to a further aspect of the method, the electrode and the current-measuring circuitry are components of an impedance measuring system and wherein the electrical current is a measure of an impedance of a heart.

According to yet another aspect of the method, the sheath has a perforation formed through its outer wall, and identifying a variation occurs while the electrode is passing by the perforation.

A plurality of electrodes may be disposed on the catheter. The method is further carried out by concurrently measuring respective electrical current in the plurality of electrodes, recognizing a transient decrease in current flow in one of the electrodes that does not fall below a lower threshold, and concluding that a position of the one electrode opposes the perforation during the transient decrease.

Responsively to identifying a variation the method is further carried out by determining a location of the distal end of the catheter relative to the perforation.

According to still another aspect of the method, the portion of the catheter is the distal end of the catheter.

According to an additional aspect of the method, the portion of the catheter is another electrode.

According to another aspect of the method, the at least one electrode includes a proximal electrode and a distal electrode. The method is further carried out by defining an upper threshold and a lower threshold, wherein moving the catheter includes iteratively advancing the catheter in the sheath while the electrical current through the distal electrode does not exceed the upper threshold, retracting the catheter in the sheath until the electrical current through the proximal electrode no longer exceeds the lower threshold, and thereafter reporting that the distal electrode is in the out-of-sheath condition and the proximal electrode is in the in-sheath condition.

According to yet another aspect of the method, defining an upper threshold and a lower threshold includes accessing a database of sheath-catheter combinations.

According to still another aspect of the method, a magnetic sensor is disposed in the catheter at a predetermined distance from the distal end, and reporting includes reading the magnetic sensor, and reporting a location of the distal end of the catheter from the reading.

There is further provided according to embodiments of the invention an apparatus, including a plurality of body surface electrodes, which are adapted to be fixed to a surface of a body at respective locations and a controller having current-measuring circuitry. The controller is adapted to be coupled to a catheter having at least one catheter electrode disposed on its distal portion and to the body surface electrodes. The controller is operative for passing electrical current through the body between the at least one catheter electrode and the body surface electrodes, and for determining position coordinates of the catheter by measuring respective characteristics of the electrical current passing through the body surface electrodes. The apparatus further includes a memory and a processor with access to the memory, the processor being cooperative with the controller for measuring the electrical current through the at least one catheter electrode with the current-measuring circuitry, identifying a variation in the electrical current between a first threshold value and a second threshold value, and responsively to the variation, reporting that a portion of the catheter has transitioned between an in-sheath condition and an out-of-sheath condition.

The apparatus may include a position processing system operative for reading signals from a magnetic sensor disposed in the catheter at a predetermined distance from the distal end of the catheter and reporting a location of the distal end of the catheter from the reading using the predetermined distance as an offset.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.
System Overview.

Figure 1:
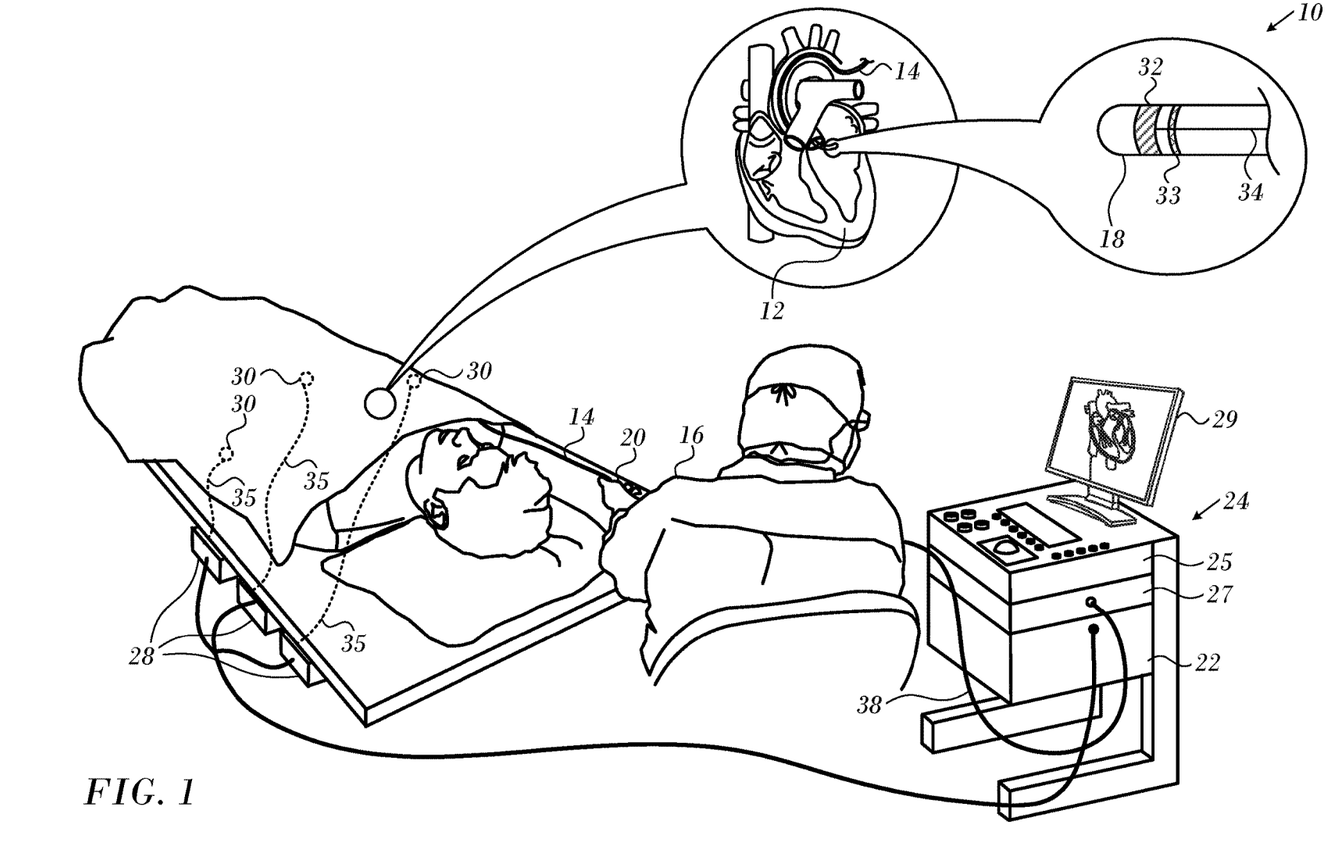
FIG. 1 is a pictorial illustration of a system for performing catheterization procedures on a heart in accordance with a disclosed embodiment of the invention.

Turning now to the drawings, reference is initially made to FIG. 1, which is a pictorial illustration of a system 10 for evaluating electrical activity and performing ablative procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall, for example, at an ablation target site. Electrical activation maps may be prepared, according to the methods disclosed in U.S. Pat. Nos. 6,226,542, and 6,301,496, and in commonly assigned U.S. Pat. No. 6,892,091, whose disclosures are herein incorporated by reference. One commercial product embodying elements of the system 10 is available as the CARTO® 3 System, available from Biosense Webster, Inc., 3333 Diamond Canyon Road, Diamond Bar, Calif. 91765. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 60° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to diagnose and treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a processor 22, located in a console 24. The processor 22 may fulfill several processing functions as described below.

Ablation energy and electrical signals can be conveyed to and from the heart 12 through one or more ablation electrodes 32 located at or near the distal tip 18 via cable 34 to the console 24. Pacing signals and other control signals may be conveyed from the console 24 through the cable 34 and the electrodes 32 to the heart 12. Sensing electrodes 33, also connected to the console 24 are disposed between the ablation electrodes 32 and have connections to the cable 34.

Wire connections 35 link the console 24 with body surface electrodes 30 and other components of a positioning sub-system for measuring location and orientation coordinates of the catheter 14. The processor 22 or another processor (not shown) may be an element of the positioning subsystem. The electrodes 32 and the body surface electrodes 30 may be used to measure tissue impedance at the ablation site as taught in U.S. Pat. No. 7,536,218, issued to Govari et al., which is herein incorporated by reference. A temperature sensor (not shown), typically a thermocouple or thermistor, may be mounted on or near each of the electrodes 32.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

In one embodiment, the positioning subsystem comprises a magnetic position tracking arrangement that determines the position and orientation of the catheter 14 by generating magnetic fields in a predefined working volume and sensing these fields at the catheter, using field generating coils 28. The positioning subsystem is described in U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. Console 24 includes a position processor 27, preferably a computer with appropriate signal processing circuits. The processor is coupled to drive a monitor 29. The signal processing circuits typically receive, amplify, filter and digitize signals from the catheter 14, including signals generated by sensors such as electrical, temperature and contact force sensors, and a plurality of location sensing electrodes (not shown) located distally in the catheter 14. The digitized signals are received and used by the console 24 and the positioning system to compute the position and orientation of the catheter 14, and to analyze the electrical signals from the electrodes.

In order to generate electroanatomic maps, the processor 22 typically comprises an electroanatomic map generator, an image registration program, an image or data analysis program and a graphical user interface configured to present graphical information on the monitor 29.

Typically, the system 10 includes other elements, which are not shown in the figures for the sake of simplicity. For example, the system 10 may include an electrocardiogram (ECG) monitor, coupled to receive signals from one or more body surface electrodes, in order to provide an ECG synchronization signal to the console 24. As mentioned above, the system 10 typically also includes a reference position sensor, either on an externally-applied reference patch attached to the exterior of the subject's body, or on an internally-placed catheter, which is inserted into the heart 12 maintained in a fixed position relative to the heart 12. Conventional pumps and lines for circulating liquids through the catheter 14 for cooling the ablation site are provided. The system 10 may receive image data from an external imaging modality, such as an MRI unit or the like and includes image processors that can be incorporated in or invoked by the processor 22 for generating and, displaying images.

Figure 2:
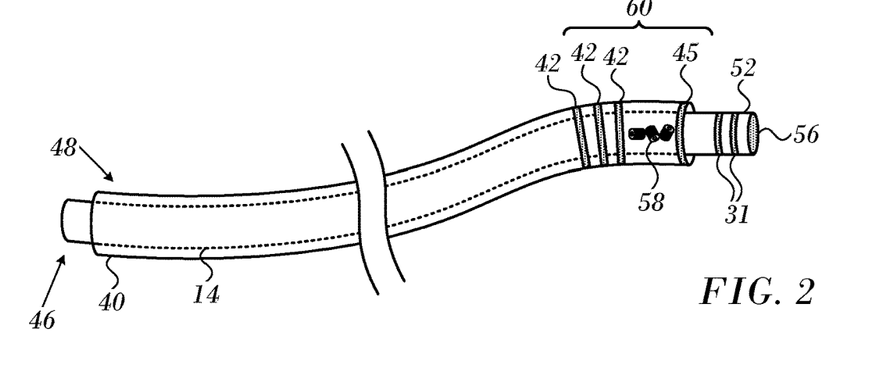
FIG. 2 is a schematic pictorial view of catheter within a sheath in accordance with an embodiment of the invention.

Reference is now made to FIG. 2, which is a schematic pictorial view of catheter 14 in sheath 40, according to an embodiment of the invention. The catheter 14 is typically a hybrid type, having electrodes 31 for impedance-based position sensing and a tri-coil magnetic sensor 58. Proximal end 46 of the catheter 14 and a proximal end 48 of the sheath 40 are both able to be manipulated by operator 16 (FIG. 1). By manipulation of their proximal ends, operator 16 is able adjust the position of sheath tip 45 relative to distal end 52 of the catheter 14, so that the sheath 40 encloses a portion of the catheter 14.

In one mode of operation, the operator first inserts sheath 40 percutaneously into the patient body and guides sheath tip 45 to the target region. The operator then inserts the catheter 14 into the lumen of the sheath 40 and guides distal end 52 through the sheath 40 to the target region (not shown). The sheath 40 may be provided with electrodes 42 for impedance-based position sensing. In such impedance-based systems, a processor in the console 24 generates and then measures a plurality of currents between at least of the electrodes 42 and a plurality of body surface electrodes, fixed at respective locations on a surface of the patient body. The processor then computes a plurality of impedances based on the measured currents and detects the position of the sheath using the computed impedances as taught in the above-noted U.S. Pat. No. 7,536,218.

While the catheter 14 is en route through the sheath 40, the sheath tip 45 may be conventionally located using imaging modalities, such as fluoroscopy, although such procedures may expose the patient to radiation.

After navigating the distal end 52 of the catheter 14 through the sheath 40, a current position map (CPM) is generated during the catheterization session during the catheterization session using impedance measurements obtained via the catheter electrodes 31 and readings from the magnetic sensor 58. One method for generation of a CPM is described in commonly assigned U.S. Pat. No. 8,478,383 to Bar-Tal et al., which is herein incorporated by reference.

In catheters having a magnetic sensor and multiple ACL electrodes, with known inter-electrode distances and offsets from the sensor, the location of all the catheter ACL electrodes can be evaluated at any time during insertion of the catheter. However, as to the sheath, until the CPM is available the impedance information provided by the sheath ACL electrodes 42 is insufficient to define the location of the sheath tip 45 with respect to physical landmarks in the heart with the precision required by a typical medical procedure. However, stability of distal portion 60 of the sheath can be assessed by monitoring readings of the sheath ACL electrodes.

It is helpful to know the precise position of sheath tip 45 in the heart. As noted above, an out-of-sheath status is required for construction of a CPM. Conventionally, however, without the CPM, it is necessary to resort to fluoroscopy or other imaging in order to obtain the position and conform the out-of-sheath status. It is desirable for the operator to have an indication of the position of catheter tip 56 relative to sheath tip 45 in order to avoid evaluating possibly invalid ACL data while the catheter is still inside the sheath as well as to acquire valid CPM data once the operator is assured that the catheter has exited the sheath.

Figure 3:
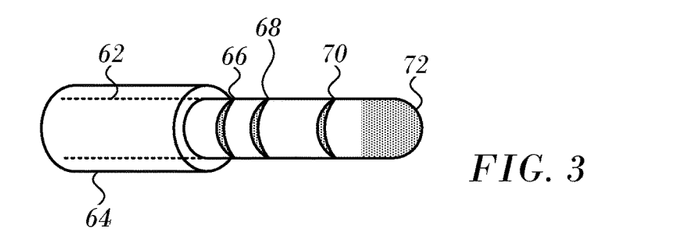
FIG. 3 is a schematic diagram illustrating a catheter having ACL electrodes and a sheath in accordance with an embodiment of the invention.

Reference is now made to FIG. 3, which is a schematic diagram illustrating a catheter 62 having electrodes extending through a sheath 64 in accordance with an embodiment of the invention. The catheter 62 in this example has three ACL electrodes 66, 68, 70 and a tip electrode 72 that is used for ablation. The catheter 62 may be provided with additional ACL electrodes (not shown). The tip electrode 72 and the electrodes 66, 68, 70 have all been extended beyond sheath tip 74, and in this configuration a CPM may be validly constructed.

Figure 4:
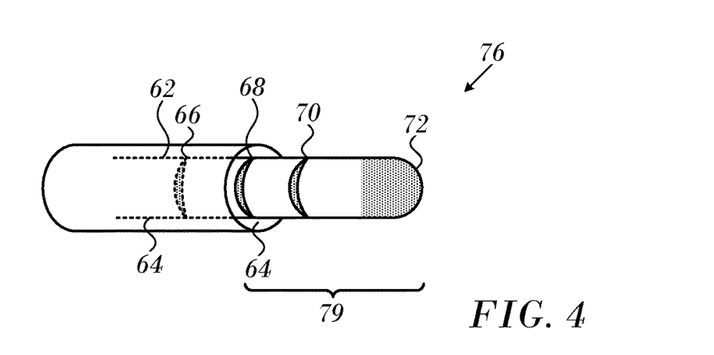
FIG. 4 is a schematic diagram illustrating a catheter lying partially within a sheath in accordance with an embodiment of the invention.

Reference is now made to FIG. 4, which is a schematic diagram illustrating catheter 62 lying partially within sheath 64 and indicating the position of catheter tip 76 relative to sheath tip 74 in accordance with an embodiment of the invention. During ablation, the physical stiffness of the sheath 64 is needed for better catheter maneuverability. In such a situation the operator may keep one or two of the most proximal ACL electrodes 66, 68 in the sheath, while the distal ACL electrode 70 and any other distal ACL electrodes (not shown) are out of the sheath. The position of the distal end of the catheter, here occupied by tip electrode 72, can be computed based on the known offsets from any of the electrodes 66, 68, 70. The presence of a short portion 78 of the catheter 62 out of the sheath enhances catheter maneuverability and stability because the sheath 64 is more rigid than the catheter 62. At the same time maintain the portion 78 outside the sheath 64 guarantees that the tip electrode 72 is also out of the sheath 64 and does not transfer energy into the sheath 64. When manipulating the catheter 62, the operator may view an indication on the monitor 29 (FIG. 1) in order to achieve the desired configuration.

The inventors have found that values of the catheter ACL electrodes currents provide discrimination between an in-sheath and an out-of-sheath status of the catheter. Several parameters influence the values:
  Electrical Impedance of human heart;
  Impedance measuring circuitry, e.g., the ACL electrical circuitry of the CARTO 3 system;
  Sheath material (including its insulative properties); and
  Sheath structure: Diameter; presence or absence of perforations; placement of perforations relative to the sheath end.

The heart may be treated as an ambient with resistance of 100-150 ohms. Under such resistance the ACL circuits yield a nominal current of 500 microamperes. When the electrode experiences a higher resistance while in a known position within the sheath, it may be assumed that some of the current is leaking via other pathways.

Without being bound by a particular theory, it would seem that when the electrode is inserted into the sheath, it is surrounded by insulative material, i.e., the sheath, and by conductive fluid but with relatively little blood. The conductive fluid can be considered to form a cylinder around the catheter. An electrical description of the model includes parasitic impedance from the sheath and from the electrical circuitry of the system. As the catheter is taken deeper into the sheath, the proportion of blood relative to the conductive fluid increases, and the parasitic impedance begins to approach the impedance of the ambient blood. Thus, some current leaks via the parasitic impedance path of the ACL electrical circuitry. Finally, as the catheter is taken even farther into the sheath, the current reading from the catheter ACL electrodes does not change as all the current follows the parasitic impedance path.

Figure 5:
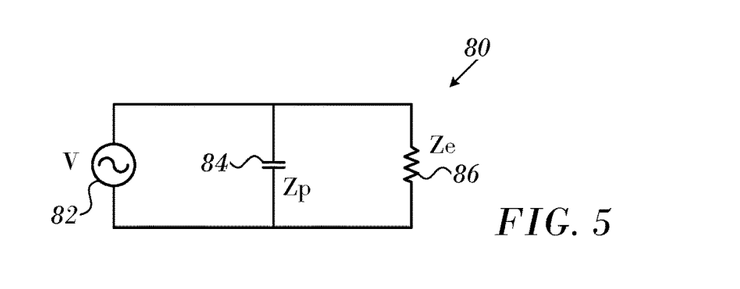
FIG. 5 is an electrical schematic of a circuit modeling the impedance and current of an ACL electrode in accordance with an embodiment of the invention.

Reference is now made to FIG. 5, which is an electrical schematic of a circuit 80 modeling the impedance and current of an ACL electrode in accordance with an embodiment of the invention. The circuit 80 comprises an alternating current generator 82 that produces a voltage V. The load of the generator 82 is a capacitor 84 having an impedance $Z_p$ in parallel with a resistor 86 having an impedance $Z_e$.

The impedance of the in-sheath electrode is given by:

$$Z_e = \frac{\rho l}{\pi(R_1^2 - R_2^2)}, \, 0 < l < l_0; \, \frac{\rho l_0}{\pi(R_1^2 - R_2^2)} + \frac{\rho(l - l_0)}{\pi(R_1^2)}, \, l_0 < l;$$

-continued
$$Z = \left(\frac{1}{Z_e} + \frac{1}{Z_p}\right)^{-1}; \, I = \frac{V}{Z}$$

where
  $R_1$ is the sheath radius;
  $R_2$ is the catheter radius;
  $\rho$ is the specific impedance of the heart;
  $l$ is the distance of the electrode from the sheath end;
  $l_0$ is the distance from the electrode to the most distal electrode;
  Z is the total system impedance;
  $Z_e$ is the ACL electrode impedance; and
  $Z_p$ is the parasitic impedance of the system.

Example 1

Experiments were performed by measuring the in-sheath and out-of-sheath currents. An aquarium was used to as a patient-simulant. The tests employed Navistar® and Thermocool® SF (7.5 F) catheters in Agilis™ (8.5 F) and MobiCath™ (8 F) sheaths. The catheters were moved in and out of the sheath in a controlled manner and the respective currents were recorded.

Figure 6:
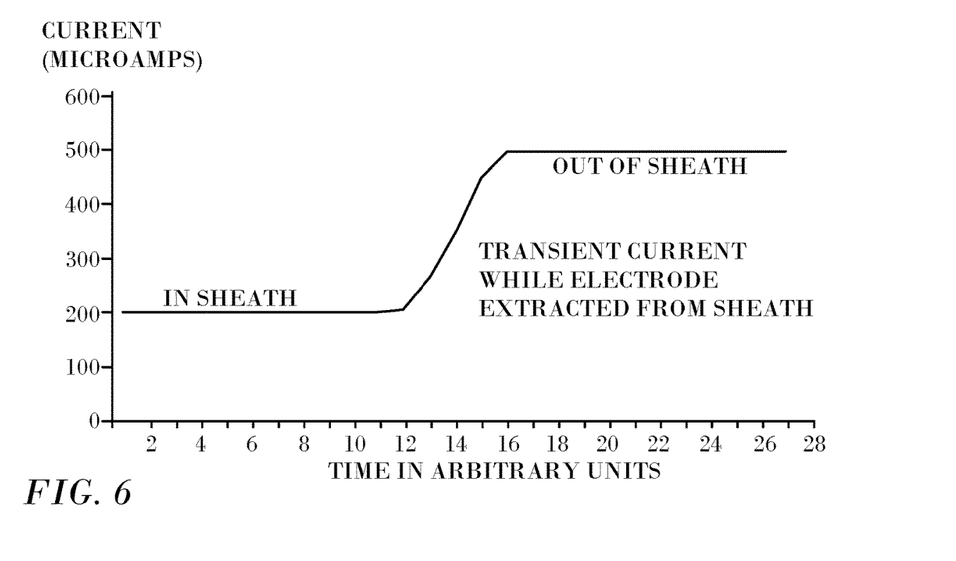
FIG. 6 is a plot of ACL electrode current obtained while an electrode transitions from an in-sheath to an out-of-sheath status accordance with an embodiment of the invention.

Reference is now made to FIG. 6, which is a plot of ACL electrode current obtained while the electrode transitions from an in-sheath to an out-of-sheath status accordance with an embodiment of the invention. The plot shows three zones of interest: (1) an in-sheath condition; (2) a transient position, in which the electrode is at the end of the sheath or partially out of the sheath; and (3) an out-of-sheath condition, in which the electrode is fully out of the sheath. Thus, the sheath is defined and identified by the historical data of the readings of the magnetic sensor during its movements.

Figure 7:
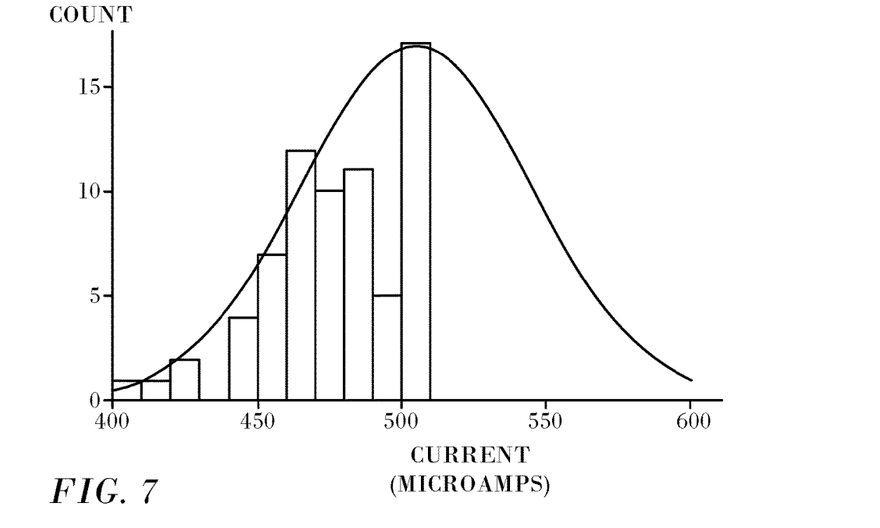
FIG. 7 is a plot showing a distribution of out-of-sheath currents in accordance with an embodiment of the invention.

A threshold value of 400 microamperes differentiates an in-sheath form an out-of-sheath condition, based on an accumulated database of recordings. Reference is now made to FIG. 7, which is a plot showing a distribution of out-of-sheath currents, in accordance with an embodiment of the invention. Each bar stands for the lowest value for all catheter electrodes while the electrodes are out-of-sheath. The current distribution can be fitted to a half Gaussian form (the nominal value is around 500 microamperes.). There is a non-zero probability in the Gaussian tail (not shown in FIG. 7) that currents as low as 400 microamperes and somewhat lower still represent out of sheath currents.

In the following examples a perforation or hole in the wall of the sheath serves as a zero point, as the hole, being a break in the insulation of the sheath, provides a highly conductive path for the electrode current. One function of the hole is to maintain the sheath clear of obstruction. Passage of an electrode by the hole produces current readings almost as high as those in an out-of-sheath condition. Nevertheless, because the distance between the hole and the sheath tip, and the offsets of the catheter tip from the electrodes are all known, the changes in current readings when the catheter electrode is abeam of the hole can be exploited to localize the catheter tip with respect to the sheath tip.

Figure 8:
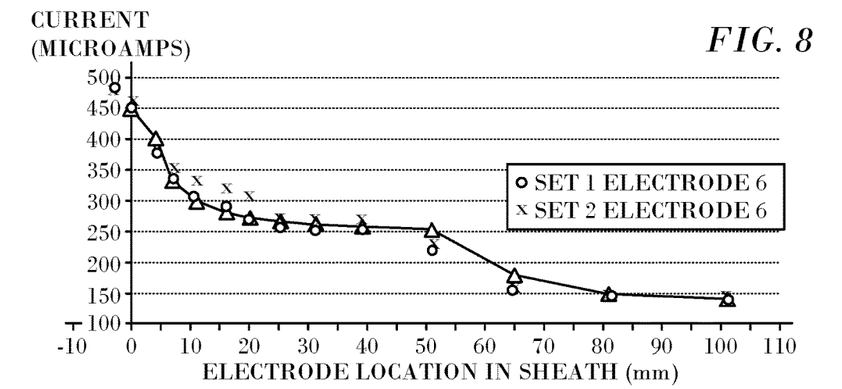
FIG. 8 is a plot of ACL electrode current as a function of penetration into a sheath in accordance with an embodiment of the invention.

Reference is now made to FIG. 8, which is a plot of ACL electrode current as a function of retraction of the catheter from an out-of-sheath condition to an in-sheath condition into a sheath in accordance with an embodiment of the invention. In this experiment a Thermocool SF (7.5 F) catheter was navigated through two different Agilis (8.5 F) sheaths. The two sets of data that were acquired are shown as open and closed triangles.

Figure 9:
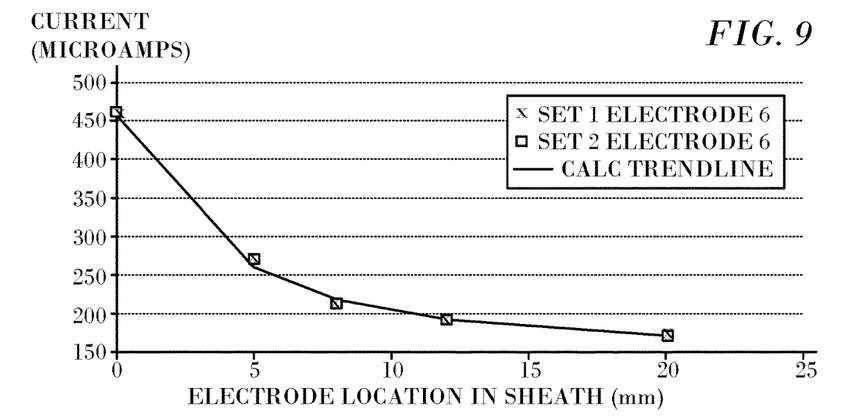
FIG. 9 is a plot of ACL electrode current as a function of penetration into a sheath in accordance with an embodiment of the invention.

Reference is now made to FIG. 9, which is a plot similar to FIG. 8, in accordance with an embodiment of the invention. In this example a Thermocool SF (7.5 F) catheter was navigated through a MobiCath (8 F) sheath. Two sets of data were acquired. It is evident that the observations are highly reproducible.

Figure 10:
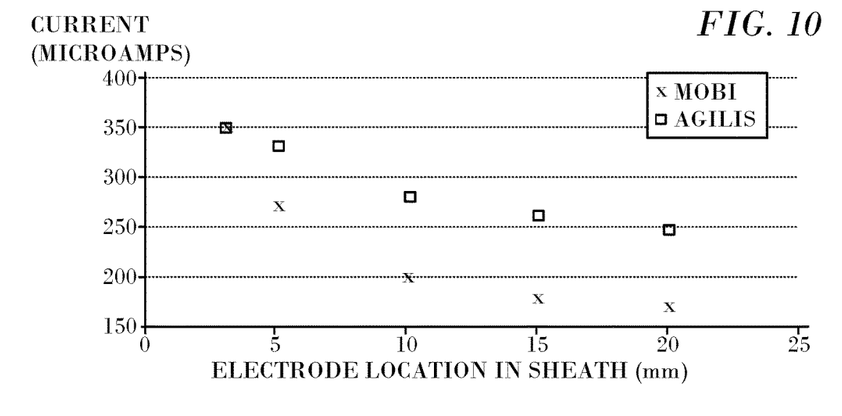
FIG. 10 is a graph comparing the data of FIG. 8 and FIG. 9 in accordance with an embodiment of the invention.

Reference is now made to FIG. 10, which is a plot comparing the results of the experiments using the Agilis (8.5 F) sheath (FIG. 8) and the MobiCath (8 F) (FIG. 9) in accordance with an embodiment of the invention. In all cases there is a relatively rapid decline (≥50%) in the first 10 mm. The decline is more rapid in the narrower MobiCath (8 F) sheath. The measurements showed good agreement with the model represented by the impedance equations given above. The different sheath-catheter combinations produce characteristic curves. Analysis of the curves by known discrimination techniques define thresholds that optimally discriminate among in-sheath and out-of-sheath conditions and the transition zone noted above. A database of such sheath-catheter combinations may be accumulated and referenced at patient sessions.

Figure 11:
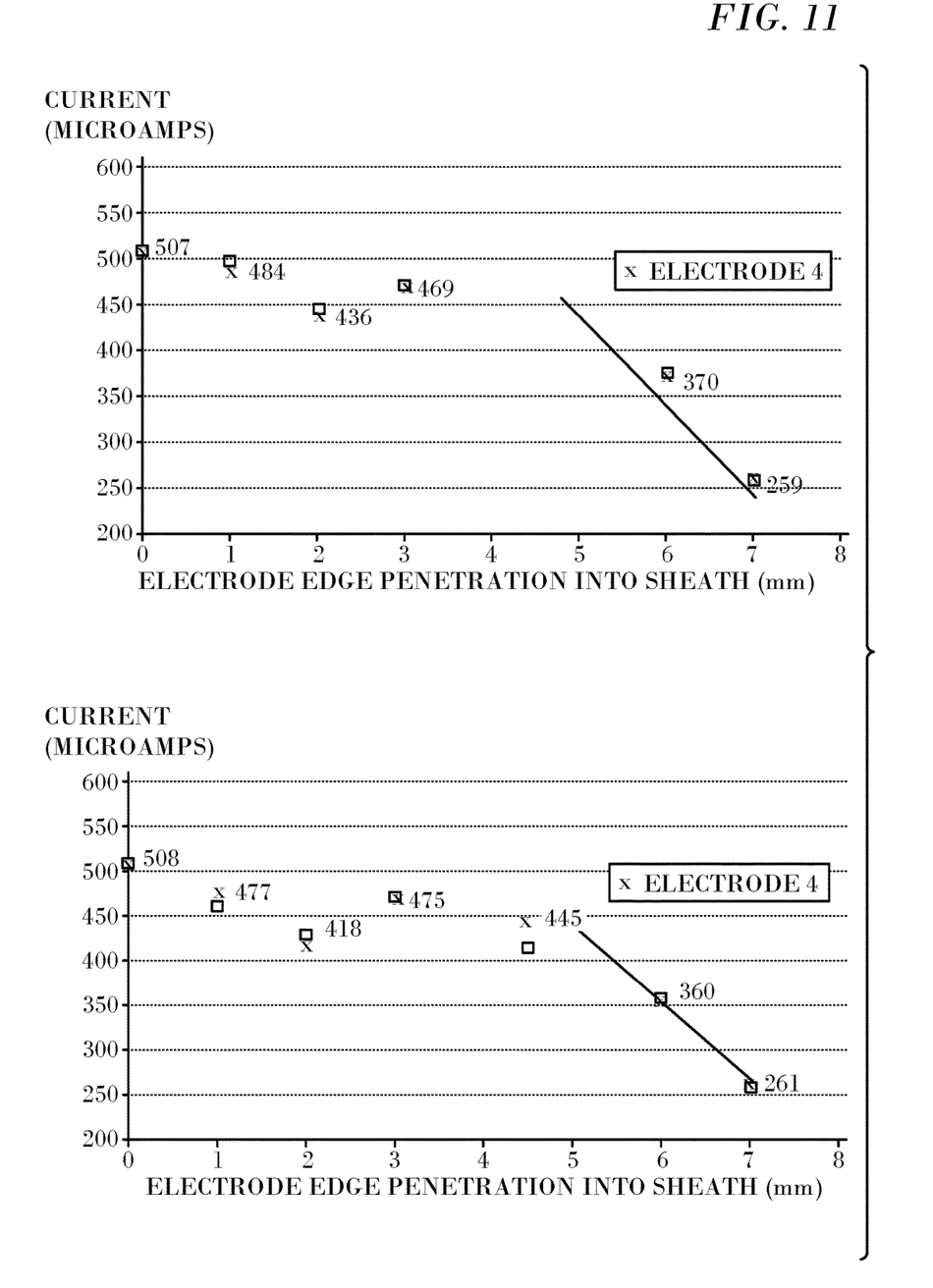
FIG. 11 displays two plots relating currents through a proximal electrode of a multi-electrode catheter to movement of the electrode into a perforated sheath in accordance with an embodiment of the invention.

Reference is now made to FIG. 11, which are two plots taken from a multi-electrode catheter as the proximal electrode is retracted into a sheath having a perforation 5 mm proximal to its distal end. The tracings show a decline at the 2 mm mark. Allowing for the width of the proximal electrode, the edge of the electrode is at 4 mm, at which point the effect of the perforation begins to be seen. Beyond the 5 mm mark the current declines. By 6 mm the electrode has passed the hole and the current has declined more than 100 μa from the baseline. At 6 mm a pre-defined threshold (400 μa) will have been crossed, after which there is a true in-sheath indication. The current decline at 2 mm can be differentiated from a true transition between an in-sheath and an out-of-sheath condition by (1) its transient nature and (2) by the level of the minimum, which exceeds the threshold value.

Example 2

Figure 12:
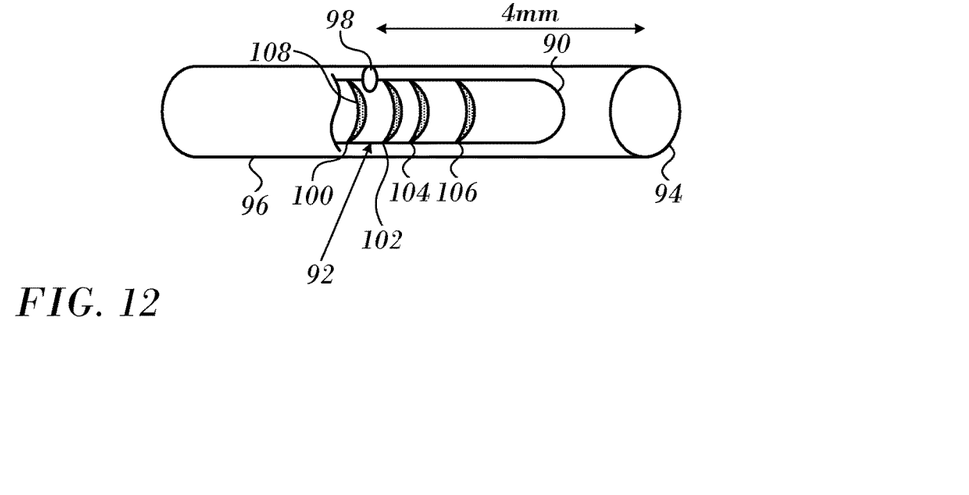
FIG. 12 is a schematic illustration of a test arrangement for determination of electrode currents in ACL electrodes in accordance with an embodiment of the invention.

Reference is now made to FIG. 12, which is a schematic illustration of a test arrangement for determination of electrode currents in ACL electrodes in accordance with an embodiment of the invention. In an initial position, tip 90 of catheter 92 lies at distal end 94 of sheath 96. A hole 98 in the sheath 96 is placed 4 mm from its distal end 94. The catheter 92 has four electrodes 100, 102, 104, 106, which are 1 mm wide.

The hole 98 enables conductive fluid, blood or salt water in the case of the test arrangement, to be in contact with the electrodes 100, 102, 104, 106 when they are within the sheath and generally opposite the hole 98. The electrodes 100, 102, 104, 106 are positioned such that in the tests, a true in-sheath indication occurs only when the distal edge 108 of electrode 100, i.e., the most proximal of the electrodes 100, 102, 104, 106, is at least 1 mm from the hole 98 in the proximal direction. As that point the current in the electrode 100 begins to rise above or is falling below the in-sheath threshold, according to whether the electrode 100 is approaching or receding from the hole 98, respectively. The electrodes 100, 102, 104, 106 are positioned on the catheter 92 such that, the most proximal electrode, electrode 100, functions as a guard: During retraction of the catheter 92, when electrode 100 passes by the hole 98 and its current begins to decline, an out-of-sheath condition cannot no longer be confirmed. Similarly, when advancing the catheter 92, a transient decline in current in the distal electrode 106 indicates that an in-sheath condition is no longer certain, as the offset between the electrode 106 and the tip 90 is such that the tip 90 is beginning to protrude through the distal end 94 of the sheath 96. At this time the location of the tip 90 and hence the location of the distal end 94 of the sheath 96 can be determined using the information from a magnetic sensor (e.g., magnetic sensor 58 as shown in FIG. 2) of the catheter 92.

In a perforated sheath, during movement of a catheter electrode into the sheath, a definitive drop in electrode current from a baseline (an out-of-sheath indication) occurs only after the electrode has crossed the hole.

In summary, in a perforated sheath, where the location of the hole is known, two points on the sheath can be determined for each catheter electrode:

the sheath end where the current rises to the steady out-of-sheath state and remains steady regardless of further distal movement of the electrode; and the location of the hole when retracting the catheter when the electrode crosses the hole, and current has declined below the in-sheath threshold.

Further inside the sheath, the electrode location can be calculated based on the above-described reference points. In the example of FIG. 12, there is a 4 mm interval of relative uncertainty between the sheath end and the hole regarding the location of a catheter electrode. However, such an electrode can still be located based on information obtained from other electrodes.

Figure 13:
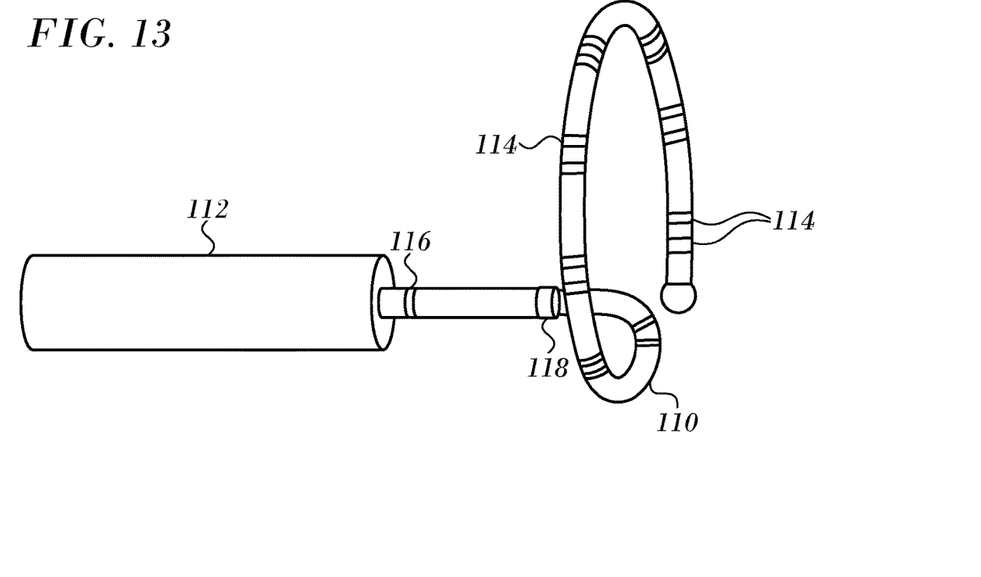
FIG. 13 is a schematic diagram of a lasso catheter, which has been inserted through a sheath in accordance with an embodiment of the invention.

Reference is now made to FIG. 13, which is a schematic diagram of a lasso catheter 110, which has been inserted through a sheath 112 in accordance with an embodiment of the invention. The lasso catheter 110 is provided with mapping electrodes 114 for building the CPM. A proximal guard electrode 116 and a distal guard electrode 118 are located on the stem of the lasso catheter 110. If it is desired only to build a CPM. It is only necessary to advance the catheter such that both the proximal and distal electrodes are positioned outside the sheath by reference only to a threshold current value. The catheter is advanced until an out-of-sheath condition is signified by the current levels in both guard electrodes 116, 118.

Figure 14:
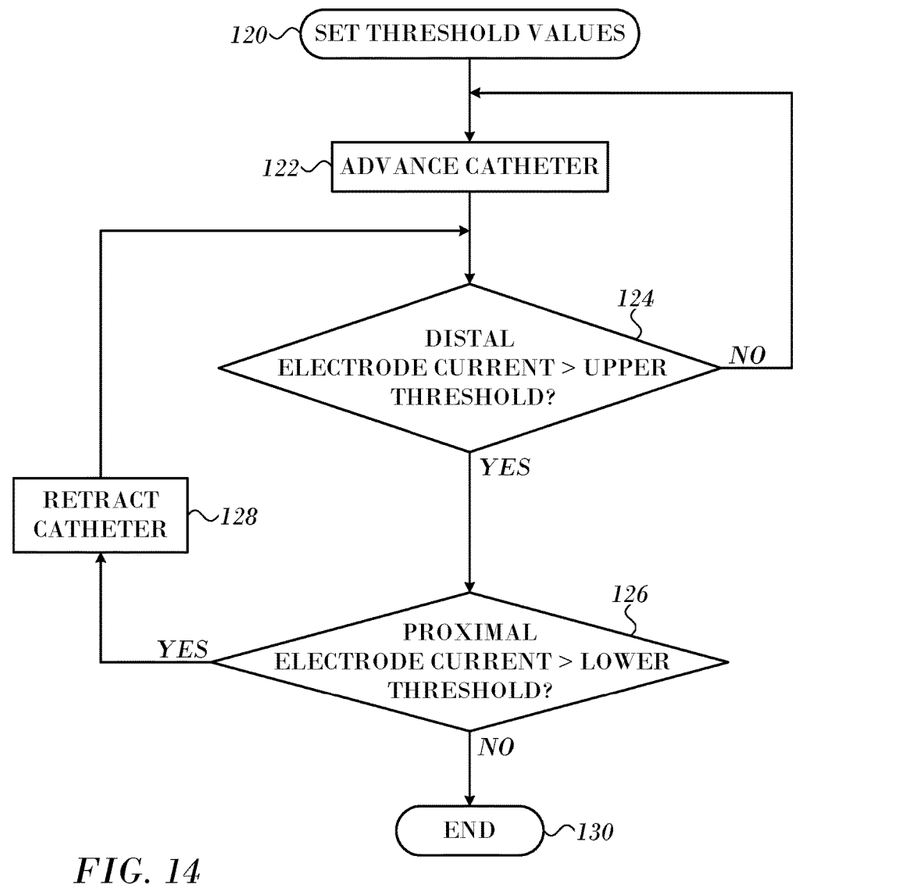
FIG. 14 is a flow chart for determining an optimum location of a catheter being inserted through a sheath in accordance with an embodiment of the invention.

It will be recalled that mechanical stability of the catheter is important when ablation is to be performed. The following procedure may be applied, mutatis mutandis, to perforated and non-perforated sheaths by appropriate positioning of the ACL electrodes. Reference is now made to FIG. 14, which is a flow chart for determining an optimum location of a catheter being inserted through a sheath in accordance with an embodiment of the invention. In this embodiment the guard electrode 118 is in an out-of-sheath condition, while the guard electrode 116 remains within the shield. Once positioned, the catheter is to be used for ablation of a target. The method is presented with reference to the example of FIG. 13.

At initial step 120 the sheath is placed conventionally into the heart. Upper and lower threshold current values are chosen according to data previously accumulated for the particular sheath and catheter being used. For example, the upper and lower threshold current values could be 400 and 250 microamperes, respectively. These values discriminate between definite in-sheath and out-of-sheath conditions and define a transitional zone therebetween.

During the following procedure, when current in a suitably positioned ACL electrode exceeds the upper threshold, the electrode is determined to be outside the sheath. Otherwise the electrode may be inside the sheath or in a transitional zone, as explained above. When the ACL electrode current is below the lower threshold, the electrode is determined to be inside the sheath. In this and subsequent flow charts some steps may be performed in different orders and not all illustrated process steps may be required to implement the method.

Next, at step 122 the catheter is advanced within the sheath. Typically, this is done in small increments when the catheter approaches the distal end of the sheath.

At decision step 124, it is determined if the current in the distal electrode (guard electrode 118; FIG. 13) exceeds the upper threshold. If the determination is negative, then the distal electrode has not yet exited the sheath. Control returns to step 122.

If the determination at decision step 124 is affirmative, then at decision step 126, it is determined if the current in the proximal electrode (guard electrode 116; FIG. 13) has risen above the lower threshold. If the determination is affirmative, then the catheter was advanced too far in the last performance of step 122. Control then proceeds to step 128. The catheter is retracted somewhat, typically less than its last advancement in step 122. Control returns to decision step 124 to redetermine its position.

If the determination at decision step 126 is negative, then the proximal electrode remains within the sheath while the distal electrode is outside the sheath. This configuration is appropriate for performing ablation. Control proceeds to final step 130, and the procedure ends.

The method of FIG. 14 may be modified for application to a multielectrode catheter when determining an optimum location of a catheter tip with respect to the sheath tip. For some ablation procedures the tolerances must be tightly controlled. For example when using a SmartTouch™ catheter, which has a contact force sensor, ACL electrodes are appropriately located with respect to the sensor in order to adjust the catheter's position such that the spring of the sensor is fully out of the sheath, while the proximal electrode is at a marginal position that still gives an in-sheath indication. For such applications a value of the upper threshold, such as 400 microamperes, may be chosen.

The procedure is performed by measuring the currents in all the electrodes concurrently, and adjusting the position of the catheter such that the current in a selected electrode, having a known offset to the tip of the catheter, is within the dynamic segment of the curve, while the current in more distal electrodes provide an out-of-sheath indication and more proximal electrodes provide an in-sheath indication. For example, referring to FIG. 8, the current value in the selected electrode should be between 250 and 400 µa in order to guarantee that the tip of the catheter protrudes through the sheath, but not more than a specified distance.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method, comprising the steps of:
    inserting a sheath into a human patient, the sheath having a lumen, an outer wall having a perforation formed therethrough and a distal end;
    moving a catheter through the lumen of the sheath, the catheter having a distal portion and at least one electrode disposed on the distal portion, the electrode being connected to current-measuring circuitry;
    measuring electrical current through the electrode with the current-measuring circuitry;
    identifying a variation in the electrical current between a first threshold value and a second threshold value while the electrode is passing by the perforation; and
    responsively to the variation, reporting that a portion of the catheter has transitioned between an in-sheath condition and an out-of-sheath condition.

2. The method according to claim 1, wherein the electrode and the current-measuring circuitry is a component of an impedance measuring system and wherein measuring electrical current comprises measuring an impedance of a heart with the electrode.

3. The method according to claim 1, wherein the at least one electrode comprises a plurality of electrodes:
    while performing the step of moving the catheter, concurrently measuring electrical current in the plurality of electrodes, respectively, wherein identifying a variation comprises recognizing a transient decrease in current flow in one of the electrodes that does not fall below a lower threshold; and
    concluding that a position of the one electrode opposes the perforation during the transient decrease.

4. The method according to claim 3, further comprising: responsively to identifying a variation determining a location of the distal end of the catheter relative to the perforation.

5. The method according to claim 1, wherein the portion of the catheter is the distal end of the catheter.

6. The method according to claim 1, wherein the portion of the catheter is another electrode.

7. The method according to claim 1, wherein a magnetic sensor is disposed in the catheter at a predetermined distance from the distal end, and reporting comprises reading the magnetic sensor, and reporting a location of the distal end of the catheter from the reading using the predetermined distance.

* * * * *